United States Patent [19]
D'Andrea

[11] Patent Number: 5,720,717
[45] Date of Patent: Feb. 24, 1998

[54] INTRACAVITARY CATHETER FOR USE IN THERAPEUTIC RADIATION PROCEDURES

[76] Inventor: Mark A. D'Andrea, P.O. Box 7894, Pasadena, Tex. 77508

[21] Appl. No.: 787,272

[22] Filed: Jan. 24, 1997

Related U.S. Application Data

[62] Division of Ser. No. 395,865, Feb. 28, 1995, Pat. No. 5,653,683.

[51] Int. Cl.[6] .............................................. A61B 17/36
[52] U.S. Cl. ............................ 604/21; 600/2; 600/3
[58] Field of Search ............................ 604/20, 21, 28, 604/49, 51, 96; 600/2, 3, 6, 7

[56] References Cited

U.S. PATENT DOCUMENTS

| | | |
|---|---|---|
| 3,861,380 | 1/1975 | Chassagne et al. |
| 4,323,055 | 4/1982 | Kubiatowicz . |
| 4,631,415 | 12/1986 | Sauerwein et al. |
| 4,733,653 | 3/1988 | Leung et al. |
| 4,861,520 | 8/1989 | van't Hooft et al. |
| 4,881,937 | 11/1989 | van't Hooft et al. |
| 4,881,938 | 11/1989 | van't Hooft . |
| 4,897,076 | 1/1990 | Puthawala ................................. 600/7 |
| 4,969,863 | 11/1990 | van't Hooft et al. ..................... 600/3 |
| 5,090,043 | 2/1992 | Parker et al. ............................ 378/121 |
| 5,106,360 | 4/1992 | Ishiwara et al. |
| 5,411,466 | 5/1995 | Hess . |
| 5,503,613 | 4/1996 | Weinberger . |

OTHER PUBLICATIONS

"Protect Delicate Pelvic Tissues with E-Z-EM Shadow-Form™ Markers for Radiation Oncology", E-Z-EM' Product Update, E-Z-EM, Inc., 1993.

"The Nucletron Difference –High Dose Rate Brachytherapy", brochure through p. 9, Nucletron Corporation, 1992.

Omnitron, "The New Generation of High Dose Rate Remote Afterloaders", brochure, Omnitron, International Inc., 1991.

"Brachytherapy Interstitial & Intracavitary Applicators & Accessories", catalog 9301, Mick Radio-Nuclear Instruments, Inc.

*Primary Examiner*—John D. Yasko
*Attorney, Agent, or Firm*—Lockwood, Alex, FitzGibbon & Cummings

[57] ABSTRACT

The present invention provides a significantly improved therapeutic tool for radiation therapy in or near body cavities accessible through existing orifices. At least one therapeutic balloon of a catheter and balloon assembly is inflated by fluid communication through the catheter. Several embodiments provide radiation therapy, at times in association with one or more of formation of seals, control of movement, nutrient passage and drainage. The radiation therapy is provided by means of rods or other radiotherapeutic items secured, positioned or inserted along the contour of the surface of the therapeutic balloon and which are thus deployed to treatment position by balloon inflation. Control of movement can be achieved through the use of a small balloon usually located where the body cavity changes size, such as at the body orifice; through the use of a template, which may be sutured to nearby tissue or secured with tether catheter assemblies inserted in other body cavities; through the use of a catheter lead which is inserted into narrow portions of a body cavity; or through the use of a secondary balloon located distally of the larger therapeutic balloon. Drainage, often required when performing this procedure in the bladder or rectum, is achieved by the use of a Foley-type catheter. Feeding, inhalation and exhalation are permitted through a communication channel within the catheter.

19 Claims, 4 Drawing Sheets

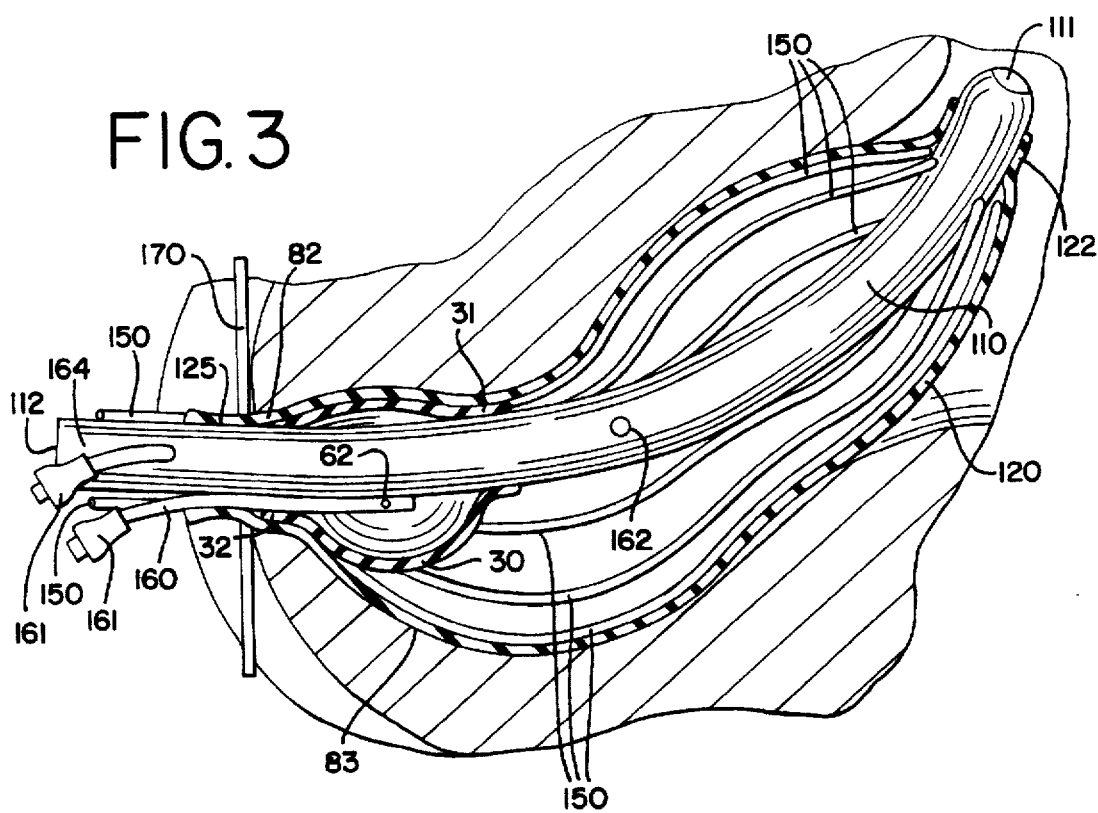
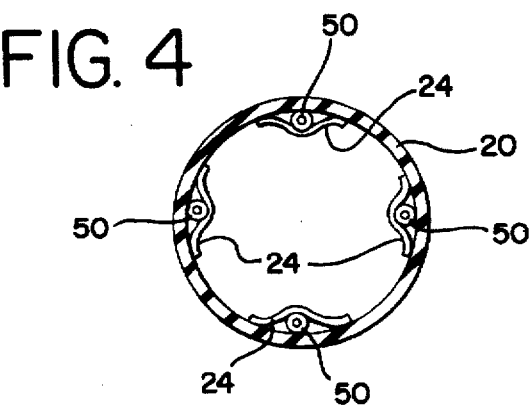
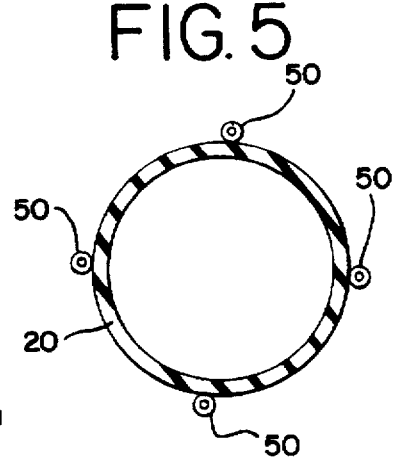
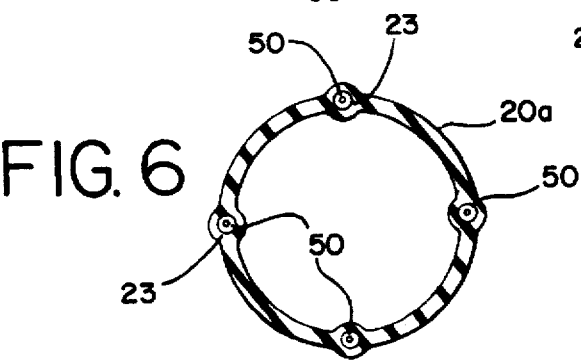

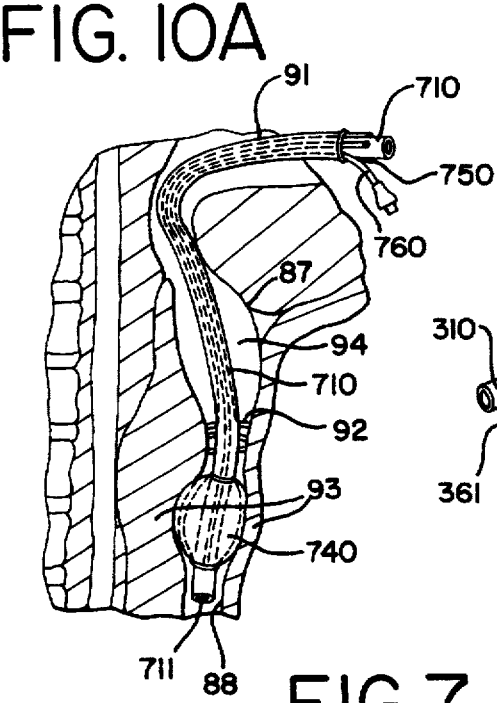
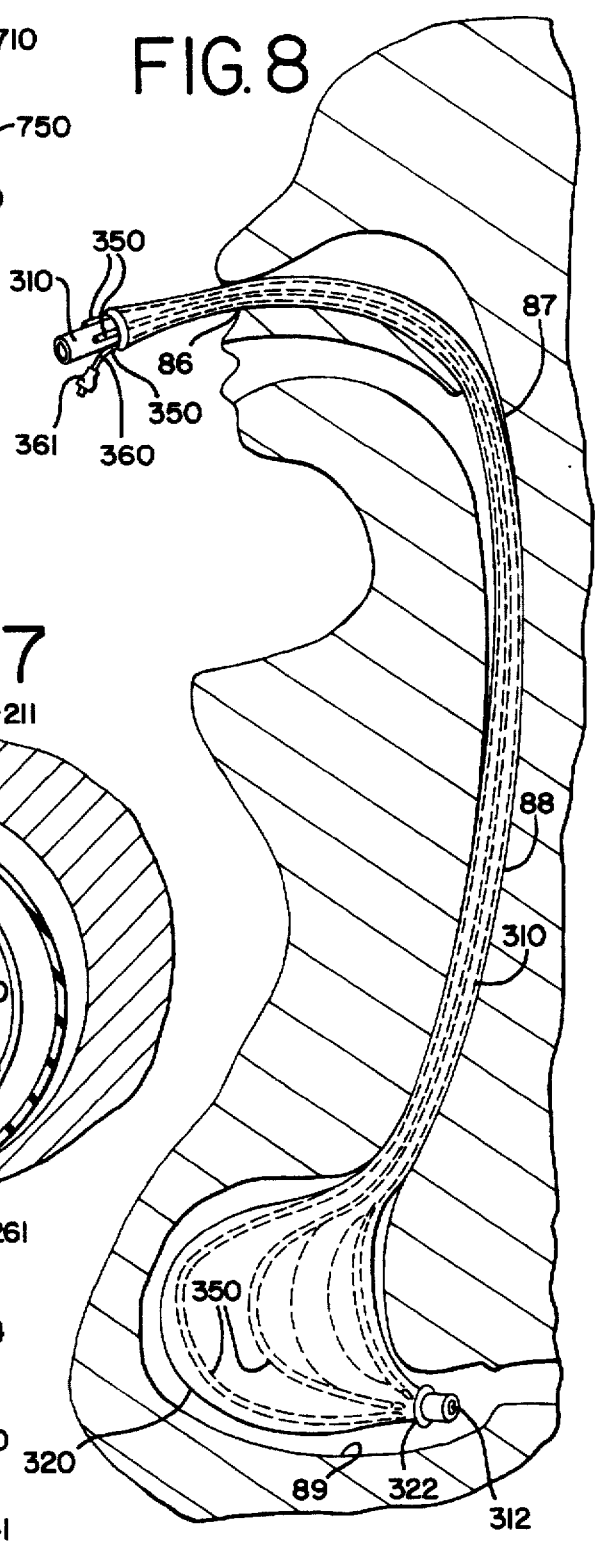
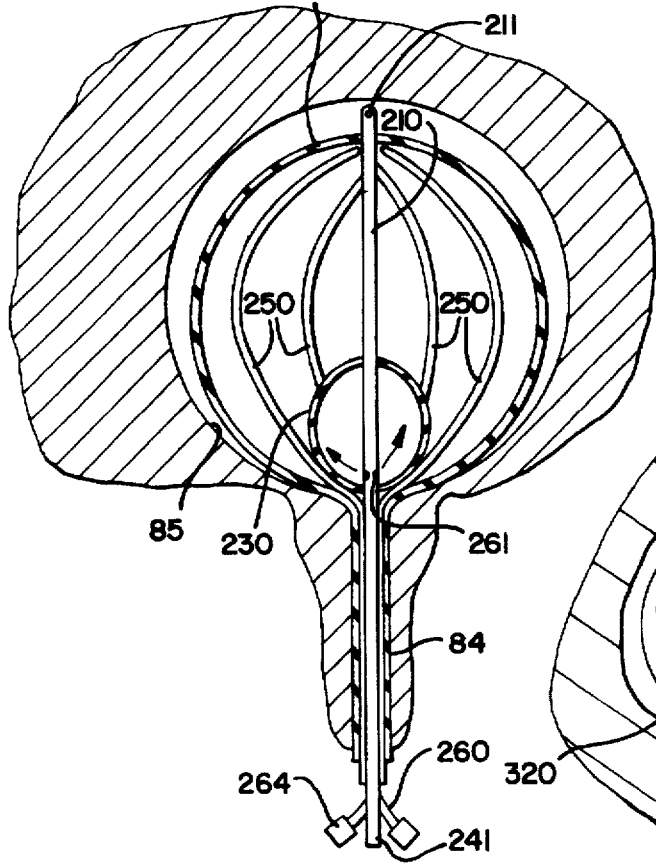

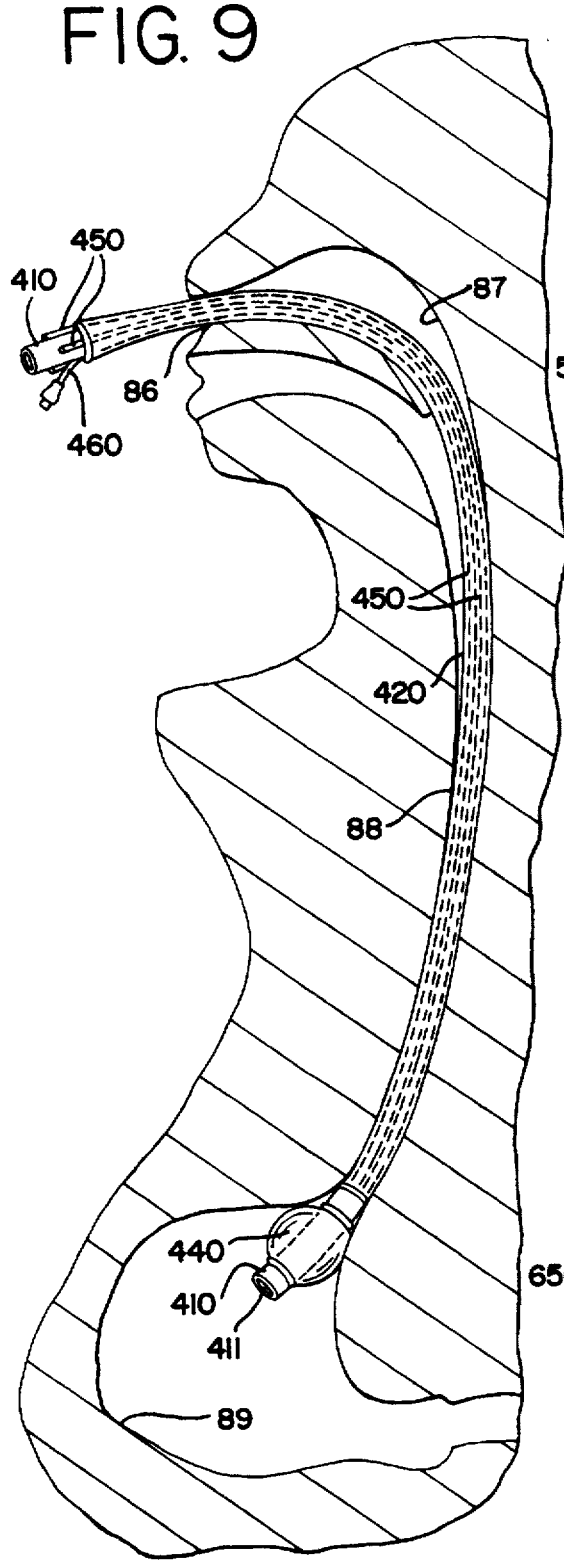
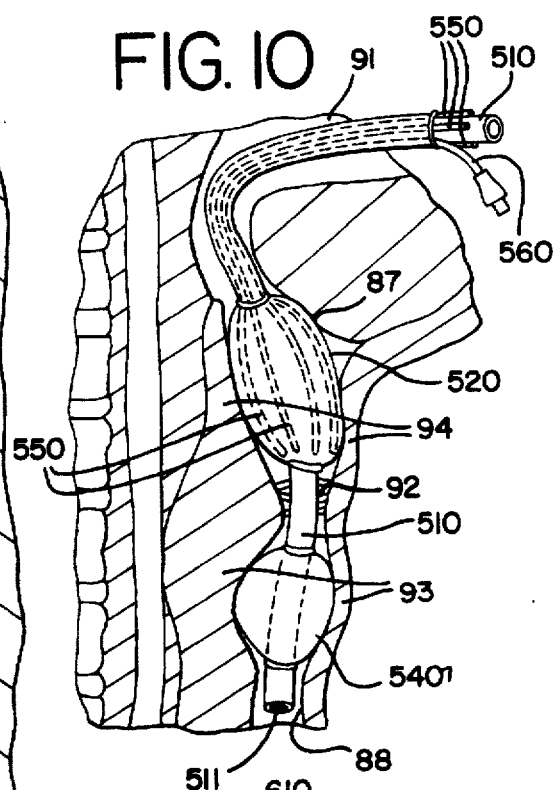
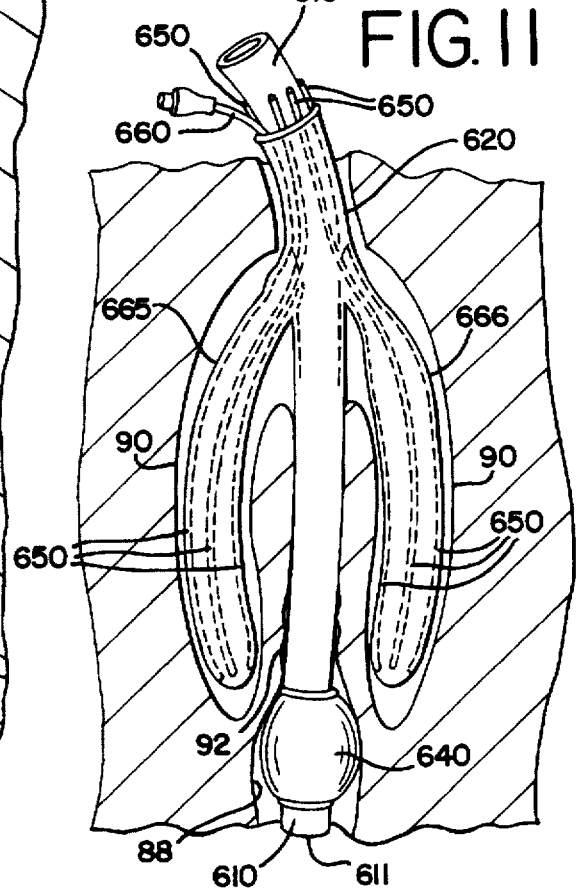
FIG. 9
FIG. 10
FIG. 11

INTRACAVITARY CATHETER FOR USE IN THERAPEUTIC RADIATION PROCEDURES

This application is a divisional of application(s) Ser. No. 08/395,865, filed Feb. 28, 1995, now U.S. Pat. No. 5,653,683.

BACKGROUND OF THE INVENTION

The present invention generally relates to therapeutic procedures and devices used during radiation therapy. This device generally consists of a catheter with a therapeutic balloon positioned along at least a portion of its length. Radiotherapeutic members, tubes or elongated rods for containing radioactive material are engaged by and move with the therapeutic balloon when it is expanded. These rods or the like may be inserted in elongated pockets of the therapeutic balloon; they may also be secured to the balloon with loops attached to the inner or outer surfaces of the balloon, or they may be secured to a balloon surface with adhesive strips. The catheter and therapeutic balloon assembly is intended to be inserted into living body cavities through existing body orifices. Once the catheter and its therapeutic balloon are inserted in the prescribed manner into the body cavity, the balloon is inflated to move and hold the radioactive material into desired radiation treatment position within the body cavity during radiation therapy. The inflated therapeutic balloon also may be used to move, push, reposition, hold or otherwise manipulate body tissue during the radiation therapy.

This invention provides the physician with a new technique to treat cancers within the body. This invention is most useful to treat cancers inside or in the proximity of body cavities including the bladder, vagina, rectum, subglottic region, stomach, bronchial tubes, nasopharynx region, and the like. This invention permits radiation treatment within the human body without requiring interstitial insertion of radiotherapeutic rods or the like. Prior to this invention, application of radiotherapeutic rods typically required insertion of the rods through tissue. This invention provides an intracavitary alternative for radiating internal body tissues. Patient trauma and risk from infection, and other similar types of potential hazards of interstitial procedures are substantially reduced. Typically, this invention can lessen the training time and/or experience level required to perform internal radiation therapy where an interstitial procedure might ordinarily be employed in view of the elimination of more intensive procedures related to an interstitial insertion of the radiotherapeutic rods.

It is a general object of this invention to provide a significantly improved tool and procedure for radiation therapy in or near body cavities accessible through existing orifices.

Another object of the invention is to provide intracavitary radiation therapy at or nearer diseased tissues than possible with external radiation therapy.

Another object of the invention is to provide radiation therapy at or nearer diseased tissues without invasive or interstitial procedures and whether at a high dose rate during short treatment times of from 15 minutes to a few hours and up to 24 hours or at a low dose rate during longer treatment times of up to about 3 days or more.

Another object of the invention is to facilitate long-term, low dose rate radiation by enabling introduction of nutrients or air or evacuation of wastes through a therapeutic treatment device itself.

Another object of the invention is to utilize existing body cavities for radiation therapy in an intracavitary manner.

Another object of this invention is to provide a device and method suitable for use in the bladder by providing an elongated insertion catheter having drainage characteristics.

Another object of this invention is to permit the physician to tailor the size of a radiation treatment device to the particular therapeutic requirements of the body cavity being treated.

Another object of this invention is to maintain the position of a therapeutic device through the use of a smaller, secondary balloon located within a larger, therapeutic balloon.

Another object of this invention is to provide a device and method suitable for use in the rectum by providing a large diameter catheter having drainage characteristics.

Another object of this invention is to provide a device and method suitable for use in the vagina or rectum by providing a template which provides securement.

Another object of this invention is to provide a device and method suitable for use in the stomach by providing a catheter having inflow and outflow characteristics.

Another object of this invention is to provide a device and method suitable for use in the subglottic region by providing a catheter having inflow and outflow characteristics.

Another object of this invention is to provide a device and method suitable for use in the nasopharynx region by providing a catheter having inhalation and exhalation characteristics.

Another object of the invention is to provide a device and method that provide for inflow of nutrients and outflow of wastes to enable long-duration treatments.

These and other objects and advantages of the present invention will be apparent from the following description.

SUMMARY OF THE INVENTION

This invention utilizes a catheter for insertion into a body cavity. A therapeutic balloon is secured to a tubular catheter body, the balloon being positioned and sized for insertion into a particular type of body cavity to be treated. The proximal end of the catheter has one or a plurality of passageways to enable fluid communication through various channels in the catheter body, depending upon the embodiment. The passageways preferably utilize one- or two-way valves, regulators, hypodermic syringes, or the like for introduction, control, and/or withdrawal of fluids into and out of one or more balloons and/or body cavities.

The fluid with which the balloon may be filled can be a biocompatible gas, such as air, or a biocompatible liquid, such as saline solution. The balloon(s) of the catheter device may also be used to move, expand, or otherwise manipulate the body cavity by balloon inflation in order to provide more effective radiation treatment.

Radiation treatment members which can take the form of rods or tubes are associated with the therapeutic balloon so as to be properly positioned by the balloon to effect the intracavitary treatment, typically by moving treatment rods toward and/or in contact with the walls of the body cavity. For example, the therapeutic balloon can contain rod receiving members which are used to hold the radiation treatment rods. The rod receiving members may be elongated pockets within the balloon material or strips of elastomeric or adhesive material along the circumference of the balloon and into which the treatment rods are inserted. Typical treatment rods contain small radioactive pellets which irradiate diseased tissue. The size, dose rate and spacing of these pellets is prescribed by the physician and assembled prior to and/or during the procedure in which the catheter device is ready for insertion through the body cavity orifice and into the body cavity.

Different embodiments of this invention can utilize one or more different approaches to secure the catheter device during radiation therapy. These include a secondary inner balloon, a secondary distal balloon, one or two secondary outer balloons and associated tether catheters, a template, and a catheter lead.

When provided, the secondary inner balloon which usually is substantially smaller than the therapeutic balloon assists in holding the catheter device in place within the body cavity at the orifice and typically is located generally within and at the proximal end of the therapeutic balloon. Upon inflation, the secondary balloon secures the catheter device within the body cavity by restricting movement of the device at the body orifice. A secondary distal balloon, when included, is located distal of the therapeutic balloon. When inflated, it anchors the catheter device at a location downstream of the therapeutic balloon.

Some embodiments lend themselves to include a template to secure the catheter device at a location external of the body cavity orifice. Such a template may be secured by one of two means: either by suturing the template to tissue in the vicinity of the orifice of the body cavity or by attaching secondary catheters which are secured in orifices near the treated body cavity. Securement may also be provided by a distally extending catheter lead which anchors the catheter device by slipping the distal end lead through a narrow section of the body cavity, such as at the cervix or duodenum. One embodiment of this invention incorporates a Foley-type catheter for radiation therapy in the bladder, said Foley-type catheter enabling the necessary drainage of urine or the like during the therapeutic procedure without having to move or remove the catheter device.

BRIEF DESCRIPTION OF THE DRAWINGS

FIG. 3 demonstrates an embodiment of the invention, shown principally in cross section, in use within the rectum, shown in cross section;

FIGS. 4–5 are cross-sectional views of the therapeutic balloon with radiation rods, demonstrating possible rod locations along the balloon contour;

FIG. 6 is a cross-sectional view showing the rod receiving members of the therapeutic balloon, demonstrating elongated pockets for therapeutic radiation rod insertion;

FIG. 7 demonstrates another embodiment of the invention, shown principally in cross section, in use within the bladder, shown in cross section;

FIG. 8 demonstrates another embodiment of the invention in use within the stomach, shown principally in cross section;

FIG. 9 demonstrates another embodiment of the invention in use within the subglottic region, shown principally in cross section;

FIGS. 10 and 10A demonstrate other embodiments of the invention in use within the nasopharynx, hypopharynx and/or subglottic region(s), shown principally in cross section; and FIG. 11 demonstrates another embodiment of the invention in use within the pyriform fossa, shown principally in cross section.

DESCRIPTION OF THE PREFERRED EMBODIMENTS

Figure 1:
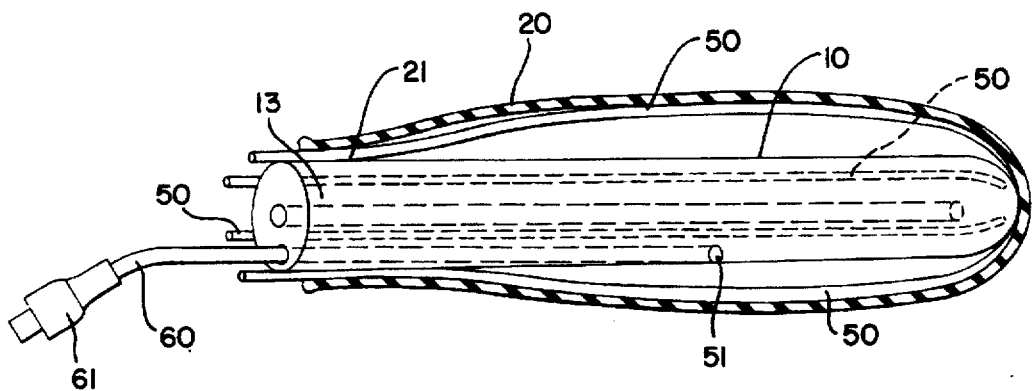
FIG. 1 is an elevation view of an embodiment of the invention, including the therapeutic balloon sealed to the catheter, inflation tube, and also radiation rods for following the contour of the balloon.

FIG. 1 shows a therapeutic balloon and catheter assembly, including a body or tube member 10, a therapeutic balloon 20, radiotherapeutic members such as the illustrated rods 50, and an inflation tube 60. The therapeutic balloon 20 is positioned over a distal end length portion of the catheter body member or cylinder 10. This distal end length portion and its therapeutic balloon 20 are intended to be inserted by the physician in an intracavitary manner through a naturally occurring body orifice of a patient and into a body cavity in order to carry out a therapeutic radiation procedure.

The therapeutic balloon 20 is typically made of a polymer material. Catheter or cylinder 10 is typically made of a polymeric material, a metallic material, or a combination of polymeric with metallic material, such as strands of metal imbedded in polymer in order to create the desired balance of flexibility and rigidity. In this particular embodiment, the catheter can be substantially rigid and is more in the nature of a plastic carrier.

Figure 2:
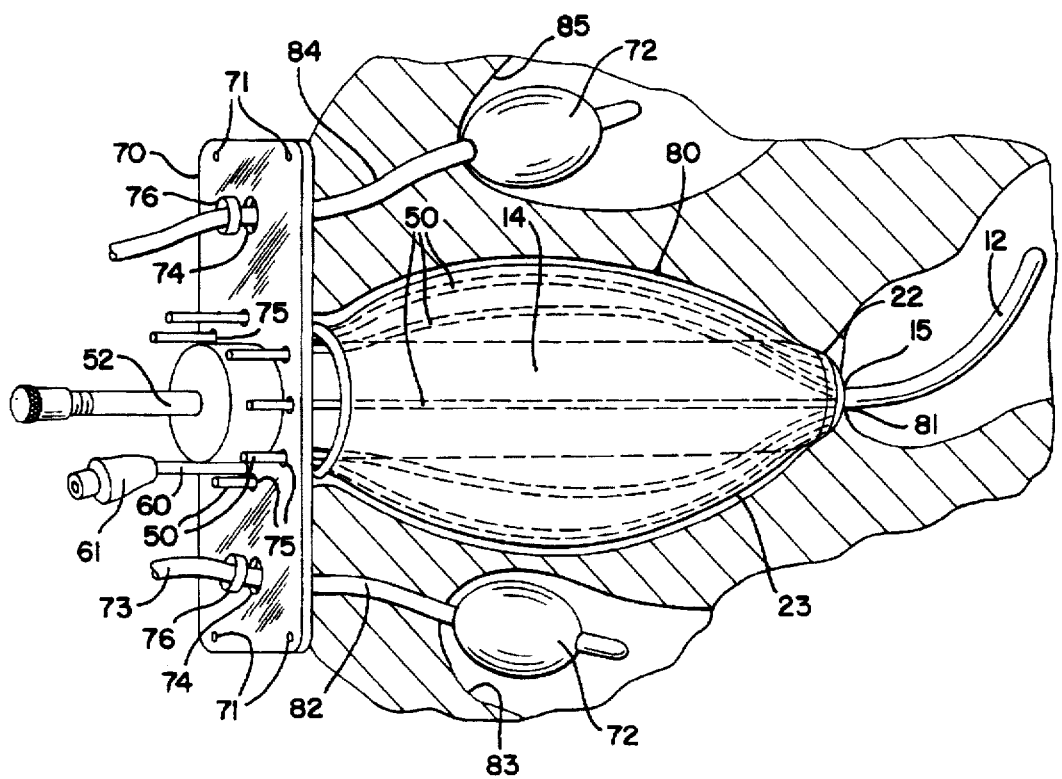
FIG. 2 demonstrates an embodiment of the invention in use within the vagina, shown in cross section.

The therapeutic balloon is inflated by means of the inflation tube 60 which opens into the balloon through an orifice 51 to inflate and deflate the balloon as desired. Inflation tube 60 may be inserted between the catheter and therapeutic balloon as illustrated in FIG. 2, or as shown in FIG. 1, it may be within the catheter or plastic carrier 10 and pass through its wall and into the balloon at 51. A proximal portion 21 of the annular inside surface of the balloon 20 is sealed about catheter or cylinder 14 at a distal annular portion 13. When an inflation tube exterior of the catheter is utilized, the seal must accommodate the profile of the tube. Fitting 61 connects with a pressurized fluid source and may include a valve or regulator. The pressurized fluid may be a biocompatible gas such as air or a biocompatible fluid such as saline solution. The means of pressurization may be a pressurized tank, an in-house line plumbed to the treatment room, a hypodermic syringe, or the like.

Typically, the radiotherapeutic rods 50 are rendered radiotherapeutic by being loaded with radioactive pellets, rice, seeds, wires or the like, as prescribed by the physician, either before or after insertion of the device into the body cavity. Any other suitable member for effecting radiotherapy may be used provided it can be moved into position by the therapeutic balloon. Positioning of the rods may be aided by rod receiving members of the therapeutic balloon skin, described in more detail in connection with FIGS. 4–6. The device may be inserted through the living body orifice into the body cavity or vessel for the therapeutic radiation procedure either prior to or following insertion of the radiotherapeutic rods into the rod receiving members. Once the assembly and radiotherapeutic rods are inserted into the cavity and secured, the balloon 20 is inflated to move the rods to the cavity or vessel wall, and radiation therapy of the diseased tissues is initiated and will continue for the prescribed duration, after which the balloon is deflated and the device removed.

FIG. 2 shows a modified form of the device of FIG. 1 in use in the vagina 80. This device further includes a template 70 and a distal end catheter tandem lead 12. The radiotherapeutic rods 50 are loaded with radioactive pellets and slipped through openings 75 in the template 70 into the rod receiving members of the therapeutic balloon 23. The device may be inserted through the vaginal opening into the vagina 80 for the treatment procedure either prior to or following insertion of the radiotherapeutic rods into the rod receiving members.

In this embodiment, the catheter is a substantially rigid cylinder 14 terminating in a substantially rigid, hemispherical section or dome 15. When provided, the catheter rigid tandem lead 12 protrudes from the dome, in which event, the balloon will not have a closed distal end as generally shown in FIG. 1, but it will have an annular connection leg 22 by which it is sealed to the cylinder end of the catheter. The rigid cylinder may have a polymeric surface and may be hollow or have passageways for loading radioactive material thereinto. When in use, the template 70 is located just outside of the body orifice and is used to hold the treatment device in position during the therapy. The template 70 is made of a polymeric or metallic material chosen for its rigidity and bored with several holes for allowing passage therethrough of the catheter and balloon assembly, radiation rods, blind end needles, and/or selected securement arrangements.

The template may be sutured into nearby tissue through holes 71. The template 70 may also be secured with anchoring balloons 72 located in the bladder 85 and/or rectum 83. The anchoring balloons 72 are located on tether catheters 73 which guide the balloons through the urethra 84 into the bladder 85 and through the anus 82 into the rectum 83, respectively, these tether catheters permitting inflation of the anchoring balloon(s) by means of passageways extending longitudinally through the catheter to a port located between the proximal and distal ends of the anchoring balloon. Fittings (not shown) are attached to the proximal ends of the catheters 73 for connection with pressurized fluid sources. The pressurized fluid may be a biocompatible gas such as air or a biocompatible fluid such as saline solution. The means of pressurization may be a pressurized tank, an in-house line plumbed to the treatment room, a hypodermic syringe, or the like. When the balloons 72 are inflated and the tether catheters 73 are secured to the template 70 at holes 74, such as with clamps 76, the device is secured in the vagina 80 for treatment without requiring suturing.

Securement of the invention also may be achieved with rigid tandem or catheter lead 12 which is intended to be inserted through the cervix 81 of the patient. The tandem or catheter lead 12 is affixed to the distal end of the catheter or cylinder 14 and may be made of a metallic or polymeric material. The tandem or catheter lead 12 may itself accommodate radiotherapeutic member(s), rod(s) and/or pellets for prescribed radiation therapy. Additional radiotherapeutic members may be loaded into internal catheter capsule 52 which can extend beyond the proximal end of the catheter or cylinder 14 as shown.

FIG. 3 shows an embodiment for use in the rectum, including a catheter 110 which usually will be more flexible than the cylinder 14 of FIG. 2. A secondary balloon 30 is positioned within the therapeutic balloon 120 having radiotherapy members such as illustrated rods 150 and inflation tubes. A template 170 can also be included. The device is inserted through the anus 82 into the rectum 83.

The secondary balloon 30 is located within the therapeutic balloon 120, being sealingly affixed at its distal portion such as by leg 31. Balloons 30 and 120 may be inflated with the same inflation tube, or tube 160 for the secondary balloon 30 isolated from tube 164 for the therapeutic balloon 120 may be provided as shown. If two inflation tubes are used, each communicates through its length to a distal port, respectively 62, 162, each port permitting inflation and deflation of each balloon. If the same inflation tube inflates both balloons, the therapeutic balloon and secondary smaller balloon are inflated by means of an inflation tube which has two isolated channels for fluid communication to the therapeutic and secondary balloons through separate ports. Fitting 161 connects with pressurized fluid sources as required. The securement or secondary balloon 30 is inflated until adequate securement is provided. Typically thereafter the therapeutic balloon 120 is inflated to move the rods 150 generally radially in an outward direction in order to bring the therapeutic radiation treatment as close as possible to the diseased tissue.

When provided, a template 170 is located just outside of the anus 82 and is used to hold the device in position during the therapy. The template 170 is bored with several holes for the catheter and balloon treatment device, for extra radiation rods, for suturing, and the like. This template arrangement may be used alone or in combination with the securement balloon, or the securement balloon alone may be used.

The catheter 110 has a hole 111 at its distal end which communicates longitudinally through the length of the catheter to an outlet 112 at the proximal end of the catheter, thereby permitting the flow of excrement from the intestines during the procedure. The hole 111, outlet 112 and the passageway with which they communicate are intended to be of cross section sufficiently large to enable flow of excrement. The opening of the hole 111 preferably is rounded to facilitate insertion in a non-traumatic fashion. The distal end of balloon 120 is sealed near the distal end of catheter 110 such as at a leg 122. Proximal end portion or leg 125 of the therapeutic balloon and, when provided, proximal leg 32 of secondary balloon 30 are sealed in pressure-resistant fashion to the catheter 110 by known procedures.

FIGS. 4–6 show three manifestations of the manner by which the radiation rods can be associated with the large therapeutic balloon of the various embodiments so as to move with the balloon and generally follow its contour when it is inflated and deflated. Arrangements for receiving the radiotherapeutic components may be provided, such as the elongated pockets 23 of the balloon 20a shown in FIG. 6. Rod receiving members may take the form of strips 24 about a portion or all of the circumference of the balloon, the strips being made of polymeric, elastomeric or adhesive material, or other arrangement such that the rod will follow the balloon movement. The objective of the radiotherapeutic component receiving members is to first restrict and then to effect movement of the radiotherapeutic components by positioning them by or onto the balloon during insertion through the orifice and into the body cavity and to bring the components or rods as near as possible to the cavity tissue. FIG. 4 shows radiotherapeutic rods located on the interior of the balloon. FIG. 5 shows radiotherapeutic rods located on the exterior of the balloon, which can avoid the need for any discrete receiving members because the rods will be pushed outwardly by the expanding balloon. FIG. 6 shows radiotherapeutic rods located within the balloon material itself. These designs provide radiation therapy along the contour of the balloon. Inflation of the balloon within and to the body cavity locates the radiation rods at the surface of the body cavity tissue.

FIG. 7 shows an embodiment for use in the bladder, including a catheter 210, a therapeutic balloon 220, secondary balloon 230, radiation rods 250, and two inflation tubes 260 and 264. The radiotherapeutic rods 250 are loaded or preloaded with radioactive pellets, rice, seeds, wires or the like as prescribed by the physician and then slipped into the rod receiving members of the therapeutic balloon. The assembly is inserted through the urethra 84 and into the bladder 85.

The proximal ends of both the secondary balloon 230 and the therapeutic balloon 220 have approximately the same location on the catheter 210. The distal end of the secondary balloon is located significantly closer to the proximal end of the catheter than the distal end of the therapeutic balloon, the distal end of the therapeutic balloon being located very near the distal end of the catheter. The secondary balloon is located and sized to provide adequate securement of the invention within the bladder.

The therapeutic balloon 220 and secondary balloon 230 are inflated by means of the inflation tubes 260 and 264, or by a single tube which has two isolated channels for fluid communication to the therapeutic and secondary balloons. The secondary balloon 230 is inflated through outlets 261 until adequate securement is provided, and the therapeutic balloon 220 is inflated to bring the therapeutic radiation treatment as close as possible to the diseased tissue.

This embodiment of the invention utilizes a Foley-type catheter 210 to enable urine flow during the therapy. The Foley-type catheter features a hole at the distal end 211 which communicates through a passageway within the catheter to a drain tube 241 located at the proximate portion of the catheter. FIG. 7 shows the male bladder, but the device is also usable in the female bladder.

FIG. 8 shows an embodiment for use of the device in the stomach. It includes an elongated catheter 310, catheter lead 312, therapeutic balloon 320, radiotherapeutic rods 350, and an inflation tube 360. The radiotherapeutic rods 350 are preloaded with radioactive pellets and then slipped into the channels of the therapeutic balloon. Catheter lead 312 guides the catheter into the mouth or the nose 86, through the nasopharynx region 87, through the subglottic region 88 and into the stomach 89. Once inserted into the prescribed location, the catheter lead 312 may be inserted into a narrow region of the stomach, such as the duodenum.

The therapeutic balloon is inflated by means of the inflation tube 360. Inflation tube 360 may be inserted between the catheter 310 and the therapeutic balloon 320. Balloon 320 is sealed about catheter 310 over inflation tube 360 at leg portion 322. Fitting 361 is for connection to a pressurized fluid source in a manner generally discussed herein or as otherwise known.

FIG. 9 shows an embodiment for use in the subglottic region. This embodiment of the invention includes an elongated catheter 410, a therapeutic balloon 420, radiotherapeutic rods 450, and inflation tube 460. The radiotherapeutic rods 450 are preloaded with radioactive pellets and then slipped into the rod receiving members of the therapeutic balloon. The assembly is inserted through the nose 86, through the nasopharynx region 87 and through the subglottic region 88 until the smaller secondary balloon 440 reaches the stomach 89.

The smaller secondary balloon 440 is located distally of the therapeutic balloon 420 at the distal end of the catheter 410 and is intended to provide securement to the device by anchoring it in the stomach 89. This secondary balloon 440 is similar in function to the secondary balloons 130 and 230 shown in FIGS. 3 and 7, respectively, but this securement or secondary balloon 440 is located outside and distal of the therapeutic balloon.

The therapeutic balloon 420 and secondary smaller balloon 440 may be inflated, for example, by means of the inflation tube 460 which has two isolated channels for fluid communication to the therapeutic and secondary balloons. The secondary balloon 440 is inflated until adequate securement is provided and the therapeutic balloon 420 is inflated to bring the therapeutic radiation treatment as close as possible to the diseased tissue at the location of the subglottic region, for example.

The catheter 410 has a hole 411 at its distal end which communicates longitudinally through the length of the catheter. The elongated longitudinal passageway which is thus provided is intended to permit the flow of nutrients and/or wastes during the radiation therapy procedure which can take several hours or even days.

FIGS. 10 and 10A illustrate embodiments for use in the nasopharynx, hypopharynx, subglottic and/or supraglottic regions. This assembly of FIG. 10 includes the catheter 510, therapeutic balloon 520, secondary balloon 540, radiotherapeutic rods 550, and inflation tube 560. The radiotherapeutic rods 550 are preloaded with radioactive pellets, rice or the like and then slipped into the rod receiving members of the therapeutic balloon 520. The assembly is inserted through the mouth or nose 91 and through the nasopharynx region 87 and past the vocal chords 92 until the smaller secondary balloon 540 reaches the subglottic region 93 proximate to the esophagus 88. At this stage, the secondary balloon 540 can be inflated to secure the device in place. Inflation of the therapeutic balloon 520 moves the radiotherapy materials outwardly to treat the supraglottic region 94.

The therapeutic balloon and secondary smaller balloon are inflated by means of one or two inflation tubes 560. The secondary balloon 540 is inflated until adequate securement is provided by its engagement in the subglottic or esophagus areas 93, 88, and the therapeutic balloon 520 is inflated to bring the therapeutic radiation treatment as close as possible to the diseased tissue. The catheter 510 has a hole 511 at its distal end which communicates longitudinally through the length of the catheter to provide a longitudinal passageway for permitting inhalation and exhalation during the radiation therapy procedure.

In the FIG. 10A embodiment, the therapeutic balloon 740 is sized, shaped and positioned for treatment of the subglottic region 740. While a secondary or securement balloon could be included for engagement in the supraglottic region 94, such is typically not required because the therapeutic balloon 740 often will adequately anchor the device. Treatment tubes 750 can extend through the tubular catheter body 710 as shown. Alternatively, the therapeutic balloon 740 can be loaded with radiotherapeutic materials prior to deployment of the device. This feature is also optional in any of the other embodiments. It can be particularly useful where the catheter is of considerable length or must bend significantly when in use, for example in the embodiments of FIG. 7 through FIG. 11. Balloon 740 inflation is through passageway 760, and fluids can pass through the catheter 710 between its proximal end and the distal opening 711.

An embodiment for use in the hypopharynx is illustrated in FIG. 11. This device includes a catheter 610, a secondary balloon 640, radiotherapeutic tubes or rods 650, and an inflation tube 660. The therapeutic balloon 620 for this embodiment may be split at a generally proximal location into two chambers 665, 666 which inflate into each pyriform fossa. The radiotherapeutic rods 650 typically are preloaded with radioactive members or materials and then positioned for movement with the balloon 620 such as by being slipped into rod receiving members of the therapeutic balloon. The therapeutic balloon is inserted into the hypopharynx 90. If needed the secondary balloon 640 can be inserted into the subglottic region. The therapeutic balloon 620 and secondary balloon 640 are inflated by means of one or two inflation tubes 660. A hole 611 and longitudinal passageway throughout the catheter 610 permit respiration during the course of the radiation therapy procedure.

It will be understood that variations of and modifications to the present invention may be made without departing from the spirit and scope of the invention.

I claim:

1. A therapeutic catheter, comprising:

a catheter body for insertion through a body orifice and into a portion of a body cavity to be subjected to radiation therapy and which will not deform under pressure from the body orifice or body cavity;

a therapeutic balloon, said therapeutic balloon having sufficient axial length and radial extendibility to generally fill the portion of the body cavity to be subjected to radiation therapy when the balloon is inflated, said therapeutic balloon having a proximal end portion and a distal end portion, said therapeutic balloon including rod receiving members, said rod receiving members being capable of receiving radiotherapeutic rods having prescribed radioactivity;

said therapeutic balloon provides manipulation of the body cavity by expansive engagement between the balloon and the body cavity upon inflation of the balloon; and an inflation tube which permits inflation and deflation of said therapeutic balloon.

2. The therapeutic catheter in accordance with claim 1, further including a securement member affixed to said catheter for securing the therapeutic catheter within the body cavity.

3. The therapeutic catheter in accordance with claim 2, wherein said securement member is a catheter lead protruding distally from the main catheter body, said lead being substantially rigid, said lead intended to be inserted through an internal orifice of the body cavity.

4. The therapeutic catheter in accordance with claim 3, wherein said catheter lead has a passageway for insertion of radiotherapeutic material thereinto.

5. The therapeutic catheter in accordance with claim 2, wherein said securement member is a template positioned near said proximal end portion of said therapeutic balloon, said template having a plurality of holes therethrough, said catheter body being located through one of said holes in the template, another of said holes of said template receiving and thereby directing at least one radiotherapeutic rod into one of the rod receiving members of the therapeutic balloon.

6. The therapeutic catheter in accordance with claim 5, further including suture holes in said template to suture the therapeutic catheter to tissue surrounding the orifice in which the therapeutic catheter is inserted to provide securement.

7. The therapeutic catheter in accordance with claim 2, wherein said securement member includes at least one anchoring catheter for insertion into a body orifice near the orifice into which the therapeutic catheter is to be inserted, said anchoring catheter having an inflatable anchoring balloon.

8. A therapeutic catheter, comprising:

a catheter body which provides sufficient rigidity for insertion into a body cavity, said catheter body having an outside surface;

a passageway longitudinally through said catheter body from its distal end to its proximal end, said passageway being large enough for permitting flow of excrement therethrough during a radiotherapeutic procedure;

a therapeutic balloon secured to a portion of the outside surface of the catheter body, said therapeutic balloon having a proximal end a distal end having at least one rod receiving member generally therebetween;

at least one radiotherapeutic rod containing a prescribed amount of radioactive material, said rod being secured to said therapeutic balloon by said rod receiving member;

said therapeutic balloon providing manipulation of the body cavity by expansive engagement between the therapeutic balloon and the body cavity upon inflation of the therapeutic balloon;

a therapeutic inflation passageway for effecting inflation and deflation of said therapeutic balloon; and said therapeutic catheter includes at least one securement member for preventing unintentional withdrawal of the therapeutic catheter during radiation treatment.

9. The catheter in accordance with claim 8, wherein said catheter body and said therapeutic balloon include respective distal ends, and said distal end of the catheter body extends distally of said distal end of the therapeutic balloon.

10. The catheter in accordance with claim 9 wherein said distal end of the catheter body includes an opening, said opening communicating through the length of the catheter body to its proximal end to permit flow of bodily wastes from the body cavity during the therapeutic procedure.

11. The catheter in accordance with claim 8, wherein said securement member is a secondary balloon positioned within said therapeutic balloon, said secondary balloon having a proximal end and a distal end defining an axial length which is substantially shorter than that of said therapeutic balloon, said secondary balloon being secured at its said proximal and distal ends to said catheter body, further including another inflation passageway for inflating and deflating said secondary balloon.

12. The catheter in accordance with claim 11, wherein said another inflation passageway is isolated from said therapeutic inflation passageway.

13. The catheter in accordance with claim 8, wherein said securement member is a template positioned near the proximal end of the therapeutic balloon, said template having at least one hole, and said catheter body and therapeutic balloon are located within the hole in the template.

14. A bifurcated therapeutic radiation catheter, comprising:

a therapeutic catheter body which is sufficiently axially rigid to permit insertion through long, narrow body cavities, said catheter body having a proximal end portion and a distal end portion;

a therapeutic balloon secured to said proximal end portion of the catheter body, said therapeutic balloon being bifurcated into two sections each sized and shaped such that when inflated each said section engages internal tissue of a hypopharynx, nasopharynx, superglottic or subglottic region and such that one said section enters one pyriform fossa and another said section enters another said pyriform fossa;

said catheter body including a longitudinal passageway communicating from said distal end portion to said proximal end portion of the therapeutic catheter body, said passageway enabling the flow of air when said therapeutic balloon the inflated within the air passageways;

a passageway which extend from the proximal end portion of the catheter body to said bifurcated balloon, said passageway communicating with each said section of said therapeutic balloon to inflate and deflate each section of said therapeutic balloon; and each said bifurcated balloon section includes a radiotherapeutic member which moves with said balloon section when it expands into engagement with said internal tissue.

15. The bifurcated therapeutic catheter in accordance with claim 14, wherein said therapeutic catheter includes an anchoring balloon at said distal end portion of the catheter body.

16. A therapeutic radiation treatment procedure comprising the steps of:

selecting a therapeutic catheter including a catheter body, a therapeutic balloon secured to the catheter body, and a passageway which permits passage of inflation fluid into and out from said balloon when it is within the body cavity to be treated;

inserting at least one radiotherapeutic member into place in engagement with the therapeutic balloon, said radiotherapeutic member containing a prescribed radioactivity;

inserting the therapeutic catheter through an orifice of a body cavity of a living patient until a desired length of the therapeutic balloon is inserted into the body cavity to provide a desired catheter penetration depth; and inflating the therapeutic balloon thus inserted until the therapeutic balloon engages internal tissue of the body cavity and thereby moving said radiotherapeutic member into position for radiation treatment.

17. The therapeutic procedure in accordance with claim 16, further including securing the catheter to a portion of the patient after said inserting step has commenced.

18. The therapeutic procedure in accordance with claim 17, wherein said selecting step includes selecting a therapeutic catheter having an anchoring balloon, and wherein said securing step includes positioning the anchoring balloon within a body cavity and thereafter inflating the anchoring balloon within this body cavity.

19. The therapeutic procedure in accordance with claim 16, further including passing fluids between the body cavity and a location exterior of the therapeutic catheter, said passing step being through the catheter body.

* * * * *